(12) United States Patent
Morrison et al.

(10) Patent No.: US 10,744,283 B2
(45) Date of Patent: Aug. 18, 2020

(54) TIDAL DRY POWDER INHALER WITH MINIATURE PRESSURE SENSOR ACTIVATION

(71) Applicant: MicroDose Therapeutx, Inc., Ewing, NJ (US)

(72) Inventors: Mark Steven Morrison, Basking Ridge, NJ (US); Douglas E. Weitzel, Hamilton, NJ (US)

(73) Assignee: MicroDose Therapeutx, Inc., Ewing, NJ (US)

( * ) Notice: Subject to any disclaimer, the term of this patent is extended or adjusted under 35 U.S.C. 154(b) by 333 days.

(21) Appl. No.: 15/507,086

(22) PCT Filed: Aug. 28, 2015

(86) PCT No.: PCT/US2015/047365
§ 371 (c)(1),
(2) Date: Feb. 27, 2017

(87) PCT Pub. No.: WO2016/033418
PCT Pub. Date: Mar. 3, 2016

(65) Prior Publication Data
US 2017/0274162 A1  Sep. 28, 2017

Related U.S. Application Data

(60) Provisional application No. 62/043,126, filed on Aug. 28, 2014.

(51) Int. Cl.
*A61M 15/00* (2006.01)
*A61M 16/00* (2006.01)

(52) U.S. Cl.
CPC ..... *A61M 15/0065* (2013.01); *A61M 15/0091* (2013.01); *A61M 2016/0036* (2013.01); *A61M 2202/064* (2013.01); *A61M 2205/50* (2013.01)

(58) Field of Classification Search
CPC .......... A61M 15/0065; A61M 2205/50; A61M 2202/064; A61M 15/0091; A61M 2016/0036; A61B 5/08
See application file for complete search history.

(56) References Cited

U.S. PATENT DOCUMENTS 4,686,638 A   8/1987  Furuse
5,694,920 A   12/1997 Abrams et al.
(Continued)

FOREIGN PATENT DOCUMENTS

CN   101112634 A   1/2008
CN   101678184 A   3/2010
(Continued)

OTHER PUBLICATIONS https://courses.lumenlearning.com/suny-ap2/chapter/the-process-of-breathing-no-content/ (Year: 2019).*

*Primary Examiner* — Bradley J Osinski
(74) *Attorney, Agent, or Firm* — Flaster Greenberg P.C.

(57) ABSTRACT

A tidal dry powder inhaler comprising: a miniature pressure sensor, a sensor port of said sensor being pneumatically coupled to a flow channel through which a user can inhale; a processor configured to process data received from a sensing element of the sensor to make a determination that inhalation of a spontaneous breath through said flow channel is in progress; a controller configured to, responsive to said determination, issue a start dosing signal; and a dosing mechanism configured to release dry powder medicament into the flow channel during inhalation of said spontaneous breath in response to receiving said signal.

20 Claims, 5 Drawing Sheets

(56) References Cited

U.S. PATENT DOCUMENTS

| | | |
|---|---|---|
| 5,839,429 A | 11/1998 | Marnfeldt et al. |
| 5,842,468 A | 12/1998 | Denyet et al. |
| 5,887,586 A | 3/1999 | Dahlback et al. |
| 6,026,809 A | 2/2000 | Abrams et al. |
| 6,152,130 A | 11/2000 | Abrams et al. |
| 6,285,731 B1 | 9/2001 | Marnfeldt et al. |
| 6,390,088 B1 | 5/2002 | Sprenger et al. |
| 6,958,691 B1 | 10/2005 | Anderson et al. |
| 6,978,780 B1 | 12/2005 | Marnfeldt et al. |
| 6,990,975 B1 | 1/2006 | Jones et al. |
| 7,072,738 B2 | 7/2006 | Bonney et al. |
| 7,151,456 B2 | 12/2006 | Godfrey et al. |
| 7,191,777 B2 | 3/2007 | Brand et al. |
| 7,198,172 B2 | 4/2007 | Harvey et al. |
| 7,233,228 B2 | 6/2007 | Lintell et al. |
| 7,249,687 B2 | 7/2007 | Anderson et al. |
| 7,347,200 B2 | 3/2008 | Jones et al. |
| 7,383,837 B2 | 6/2008 | Robertson et al. |
| 7,424,888 B2 | 9/2008 | Harvey et al. |
| 7,495,546 B2 | 2/2009 | Lintell et al. |
| 7,837,648 B2 | 11/2010 | Blair et al. |
| 7,896,006 B2 | 3/2011 | Hamano et al. |
| 8,231,573 B2 | 7/2012 | Edwards et al. |
| 8,240,301 B2 | 8/2012 | Spaargaren et al. |
| 8,424,517 B2 | 4/2013 | Sutherland et al. |
| 8,464,707 B2 | 6/2013 | Jongejan et al. |
| 8,547,239 B2 | 10/2013 | Peatfield et al. |
| 8,807,131 B1 | 8/2014 | Tunnell et al. |
| 8,960,189 B2 | 2/2015 | Morrison et al. |
| 8,997,735 B2 | 4/2015 | Zierenberg et al. |
| 9,056,174 B2 | 6/2015 | Bradshaw et al. |
| 9,174,009 B2 | 11/2015 | Peatfield et al. |
| 9,188,579 B2 | 11/2015 | Shen et al. |
| 9,242,056 B2 | 1/2016 | Andersen et al. |
| 9,339,616 B2 | 5/2016 | Denny et al. |
| 9,364,619 B2 | 6/2016 | Overfield et al. |
| 9,427,534 B2 | 8/2016 | Bruin et al. |
| 9,463,291 B2 | 10/2016 | Imran et al. |
| 9,468,729 B2 | 10/2016 | Sutherland et al. |
| 9,550,031 B2 | 1/2017 | Van Sickle et al. |
| 9,694,147 B2 | 7/2017 | Peatfield et al. |
| 9,736,642 B2 | 8/2017 | Ostrander et al. |
| 9,839,398 B2 | 12/2017 | Yamamori et al. |
| 9,884,157 B2 | 2/2018 | Weitzel et al. |
| 9,911,308 B2 | 3/2018 | Edwards et al. |
| 9,956,360 B2 | 5/2018 | Germinario et al. |
| 9,962,507 B2 | 5/2018 | Germinario et al. |
| 9,962,508 B2 | 5/2018 | Bruin et al. |
| 10,016,134 B2 | 7/2018 | Hansen et al. |
| 10,046,121 B2 | 8/2018 | Kolb et al. |
| 2002/0185128 A1 | 12/2002 | Theobald et al. |
| 2003/0079744 A1* | 5/2003 | Bonney ............ A61M 15/0028 128/203.12 |
| 2003/0192535 A1 | 10/2003 | Christrup et al. |
| 2004/0050385 A1* | 3/2004 | Bonney ............ A61M 15/0065 128/203.15 |
| 2004/0089299 A1 | 5/2004 | Bonney et al. |
| 2004/0117062 A1 | 6/2004 | Bonney et al. |
| 2005/0119604 A1 | 6/2005 | Bonney et al. |
| 2005/0161467 A1 | 7/2005 | Jones et al. |
| 2005/0183725 A1 | 8/2005 | Gumaste et al. |
| 2005/0247312 A1 | 11/2005 | Davies et al. |
| 2005/0251289 A1 | 11/2005 | Bonney et al. |
| 2007/0076067 A1 | 4/2007 | Hamano et al. |
| 2007/0111365 A1 | 5/2007 | Tateishi et al. |
| 2008/0230057 A1 | 9/2008 | Sutherland et al. |
| 2009/0090361 A1 | 4/2009 | Gumaste et al. |
| 2009/0114219 A1* | 5/2009 | Ferris ............ A61M 15/0065 128/203.15 |
| 2009/0221308 A1 | 9/2009 | Lerner et al. |
| 2010/0071696 A1 | 3/2010 | Jafari et al. |
| 2010/0089394 A1* | 4/2010 | Sakurada ............ A61B 5/087 128/203.14 |
| 2010/0242960 A1 | 9/2010 | Zangerle et al. |
| 2010/0250280 A1 | 9/2010 | Sutherland et al. |
| 2011/0043357 A1* | 2/2011 | Peatfield ............ A61M 5/1413 340/522 |
| 2011/0282693 A1 | 11/2011 | Craft et al. |
| 2012/0042731 A1 | 2/2012 | Lin et al. |
| 2013/0269685 A1 | 10/2013 | Wachtel et al. |
| 2013/0298905 A1 | 11/2013 | Levin et al. |
| 2014/0106324 A1 | 4/2014 | Adams et al. |
| 2014/0182584 A1 | 7/2014 | Sutherland et al. |
| 2014/0283831 A1* | 9/2014 | Foote ............ A61M 16/0051 128/204.19 |
| 2015/0283341 A1 | 10/2015 | Adams et al. |
| 2016/0082208 A1 | 3/2016 | Ballam et al. |
| 2016/0128389 A1 | 5/2016 | Lamb et al. |
| 2016/0166766 A1 | 6/2016 | Schuster et al. |
| 2016/0228657 A1 | 8/2016 | Sutherland et al. |
| 2016/0256639 A1 | 9/2016 | Van Sickle et al. |
| 2016/0314256 A1 | 10/2016 | Su et al. |
| 2017/0079557 A1 | 3/2017 | Lauk et al. |
| 2017/0109493 A1 | 4/2017 | Hogg et al. |
| 2017/0140125 A1 | 5/2017 | Hogg et al. |
| 2017/0164892 A1 | 6/2017 | Sezan et al. |
| 2017/0173279 A1 | 6/2017 | Sutherland et al. |
| 2017/0246406 A1 | 8/2017 | Sutherland et al. |
| 2017/0258993 A1 | 9/2017 | Pizzochero et al. |
| 2017/0262613 A1 | 9/2017 | Ljungberg et al. |
| 2017/0325734 A1 | 11/2017 | Sutherland et al. |
| 2017/0363673 A1 | 12/2017 | Mukherjee et al. |
| 2018/0011988 A1 | 1/2018 | Ziegler et al. |
| 2018/0052964 A1 | 2/2018 | Adelson et al. |
| 2018/0085540 A1 | 3/2018 | Dantsker et al. |
| 2018/0125365 A1 | 5/2018 | Hunter et al. |
| 2018/0161530 A1 | 6/2018 | Ganton et al. |

FOREIGN PATENT DOCUMENTS

| | | |
|---|---|---|
| EP | 667168 A1 | 8/1995 |
| EP | 1135056 B1 | 8/2006 |
| EP | 1992381 A1 | 11/2008 |
| EP | 2357015 A2 | 8/2011 |
| EP | 3228345 A1 | 10/2017 |
| JP | S-60-86946 | 6/1985 |
| JP | S 61-167168 A | 7/1986 |
| JP | 2004-508899 A | 3/2004 |
| JP | 2007-097787 A | 4/2007 |
| JP | 2007-152546 A | 6/2007 |
| JP | 2007-523700 A | 8/2007 |
| JP | 2008-534209 A | 8/2008 |
| JP | 2008-301847 A | 12/2008 |
| JP | 2012-503527 A | 2/2012 |
| JP | 2012-042460 A | 3/2012 |
| JP | 2012228415 A | 11/2012 |
| JP | 2013516558 A1 | 5/2013 |
| WO | WO/1995/022365 A1 | 8/1995 |
| WO | WO/1999/063901 A1 | 12/1999 |
| WO | WO 02-24264 A1 | 3/2002 |
| WO | WO/2003/063754 A1 | 8/2003 |
| WO | 2005/081977 A2 | 9/2005 |
| WO | WO 2006-106367 A1 | 10/2006 |
| WO | 2008/149959 A1 | 12/2008 |
| WO | WO/2009/003989 A1 | 1/2009 |
| WO | 2010/036653 A1 | 4/2010 |
| WO | WO 2011090522 A1 | 7/2011 |
| WO | WO/2016/043601 A1 | 3/2016 |
| WO | WO/2017/005605 A1 | 1/2017 |
| WO | WO/2017/051389 A1 | 3/2017 |
| WO | WO/2017/129521 A1 | 8/2017 |
| WO | WO/2017/141194 A1 | 8/2017 |
| WO | WO/2017/176693 A1 | 10/2017 |
| WO | WO/2017/176704 A1 | 10/2017 |
| WO | WO/2017/180980 A1 | 10/2017 |
| WO | WO/2017/189712 A1 | 11/2017 |
| WO | WO/2018/128976 A1 | 7/2018 |
| WO | WO/2018/134552 A1 | 7/2018 |
| WO | WO/2018/134553 A1 | 7/2018 |

\* cited by examiner

TIDAL DRY POWDER INHALER WITH MINIATURE PRESSURE SENSOR ACTIVATION

This application is the National Stage Entry under 35 U.S.C. § 371 Patent Cooperation Treaty Application No. PCT/US2015/047365, filed Aug. 28, 2015, which claims the benefit of United States Provisional Application No. 62/043,126 filed on Aug. 28, 2014, the contents of which are incorporated fully herein by reference.

The present disclosure generally relates to an inhaler, for example for medicament administration. More particularly, the disclosure relates to the use of a miniature pressure sensor for inhalation detection in a tidal dry powder inhaler.

Inhalation and/or exhalation detection is often required in diagnosis and treatment of lung conditions, with such devices as peak flow meters and spirometers often being used.

A spirometer is an apparatus for measuring the volume of air inspired and expired by a patient's lungs. Spirometers measure ventilation, the movement of air into and out of the lungs. From the traces, known as spirograms, output by spirometers, it is possible to identify abnormal (obstructive or restrictive) ventilation patterns. Existing spirometers use a variety of different measurement methods including pressure transducers, ultrasonic and water gauge.

Inhalers or puffers are used for delivering medication into the body via the lungs. They can be used, for example, in the treatment of asthma and chronic obstructive pulmonary disease (COPD). Types of inhalers include metered dose inhalers (MDIs), dry powder inhalers (DPIs) and nebulisers.

Modern breath controlled nebulisers generally fall into one of two categories: breath enhanced or breath actuated. Breath enhanced nebulisers use patient airflow to control the flow of drug-containing aerosol to the patient. Since aerosol is generated continuously in these nebulisers, some is wasted to the environment. Breath actuated nebulisers use inhalation and/or exhalation detection to turn the aerosol generator on and off with patient breathing. This improves efficiency compared to breath enhanced nebulisers, since little if any drug is lost to the environment. Detection in breath actuated devices is usually by heat and/or pressure sensors.

In order to monitor the flows associated with tidal (spontaneous) breathing, a pressure sensor is most convenient because pressure information can be used to determine flow, which can then be used to determine volume.

Pressure sensors used for breath detection generally measure the pressure difference across a section of the airway through which a patient breathes. This is commonly done using two connections, by tubing or other suitable conduits, to connect the sensor to said airway. It is also possible to use a single connection to the airway, with the other port open to the atmosphere. A single port gauge type sensor can also be used if the pressure within the airway is measured both before and after flow is applied, the difference in readings representing the desired pressure drops across the air path resistance. However, the uncertainty associated with the first (no flow) reading is generally high.

Regardless of the pressure sensor type used, pressure sensors are generally connected to patient airways using flexible tubing. A disadvantage of such systems is the possibility of sensor damage related to fluid contamination in the form of spilled drug or patient secretions (mucous, sputum, etc.). In order to isolate the pressure sensor from such contaminants, manufacturers often locate the pressure sensor some distance from the measurement site using elastomeric tubing. However, liquids may still condense within the tubing, creating an environment for bacterial growth in areas exposed to the patient but not generally accessible for cleaning.

Another problem with conventional pressure sensors is thermal drift; the phenomenon by which the pressure reading can change over time with changes in local temperature. It is possible to compensate for such drift using additional circuitry, but this adds cost and volume and increases power requirements. Such circuitry can be located within the pressure sensor itself, but considering that the sensor is generally somewhat removed from the gas being measured, the temperature detected may not be representative of that gas. The temperature monitoring circuitry could be located at the patient, but this adds additional components, plus cost and complexity.

Yet another problem with conventional pressure sensors is susceptibility to high radio frequency (RF) exposure. This can be a real issue when operating in close proximity to a radio transmitter, such as a mobile phone. Other potential sources include wireless communications devices, such as Wi-Fi routers and cordless phones, and various other forms of information technology (IT) equipment such as wirelessly networked printers.

Another issue with some conventional pressure sensors is hysteresis, the reluctance of a pressure sensing material such as a diaphragm to return to its original form, shape or position after being deformed. This is observed as a difference in output when passing through the same pressure from different directions (either from above or below the target pressure). When dealing with very low pressure changes, such an offset can be large enough to mask the signal being measured.

Sensors used for tidal breath detection (for example in nebulizers or devices with non-vented facemasks or mouthpieces, especially when used with infants or patients with compromised respiration) typically cover the range from 0 to 10 kPa, with only the very low end of that range (e.g. from 0 to 200 Pa) actually being used. Hysteresis effects can be prominent in this range because the sensor is forced to transition from a state of no stress (at 0 Pa) to a state of stress (at >0 Pa). As such, when pressure is first applied, the sensor may not provide a linear response, or may exhibit less than optimum sensitivity, until this stress is overcome.

However, with the miniaturisation of components, miniature pressure sensors such as microelectromechanical system (MEMS) pressure sensors and nanoelectromechanical system (NEMS) pressure sensors have been developed. MEMS pressure sensors are starting to be used in respiratory applications.

There are described herein new means of activating dry powder inhalers which avoid some or all of the abovementioned disadvantages.

According to a first aspect, there is provided a tidal dry powder inhaler comprising: a miniature pressure sensor, a sensor port of said sensor being pneumatically coupled to a flow channel through which a user can inhale; a processor configured to process data received from a sensing element of the sensor to make a determination that inhalation of a spontaneous breath through said flow channel is in progress; a controller configured to, responsive to said determination, issue a start dosing signal; and a dosing mechanism configured to release dry powder medicament into the flow channel during inhalation of said spontaneous breath in response to receiving said start dosing signal.

The miniature pressure sensor could be a microelectromechanical system (MEMS) pressure sensor or a nanoelectromechanical system (NEMS) pressure sensor.

The processor could be configured to make the determination when said data received from said sensing element indicates that air flow rate in the flow channel has reached a predetermined start dosing threshold value. Said predetermined threshold value could be less than 50%, for example between 30 and 35%, for example 32%, of a predetermined peak inspiratory flow (PIF) rate value.

Said dosing mechanism could be configured to release drug in discrete time packets. Said discrete time packets could have a duration of approximately 50 ms to approximately 500 ms, for example approximately 50 ms to approximately 200 ms, preferably approximately 100 ms to approximately 200 ms, most preferably approximately 100 ms.

Said processor could be further configured to, subsequent to making the determination that inhalation of a spontaneous breath through said flow channel is in progress, process data received from said sensing element to make a determination that a target volume of the user's lungs has been filled. Said controller could be further configured to, responsive to said determination that a target volume of the user's lungs has been filled, issue a stop dosing signal. The dosing mechanism could be further configured to stop releasing dry powder medicament into the flow channel in response to receiving said stop dosing signal.

The processor could be configured to make the determination that a target volume of the user's lungs has been filled when said data received from the sensing element indicates air flow rate in the flow channel, averaged over time, is at a predetermined stop dosing threshold value.

The inhaler could comprise a reusable part and a replaceable drug cartridge. Said reusable part could comprise electronic cartridge identification means. Said electronic cartridge identification means could be implemented by direct connection or using a wireless technique. Direct connections could include logic such as pull-up resistors or jumpers or non-volatile memory such as Electrically Erasable Programmable Read-Only Memory (EEPROM) or Flash that can be read by the reusable part. Wireless connections can include BLE, or Near Field Communications (NFC) e.g. Radio Frequency Identifier (RFID) tags.

The sensor could be a MEMS barometric pressure sensor. The sensor could be a piezo-resistive MEMS pressure sensor or a capacitive MEMS pressure sensor.

Said processor could be comprised in the sensor.

The inhaler could further comprise a wireless transmitter or transceiver coupled to said processor.

The inhaler could have a spirometer function.

The sensor could be located inside the flow channel. The sensor could be located in a recess in an internal wall of the flow channel.

The sensor could be located external to the flow channel. Said sensor port could be pneumatically coupled to the flow channel via an opening in a wall of the flow channel. The inhaler could further comprise a seal arranged to pneumatically couple the sensor port to said opening. At least a part of said seal could be sandwiched between the sensor and the wall. At least a part of said seal could extend from an exterior surface of said wall to a surface on which the sensor is mounted so as to encapsulate the sensor in a pneumatic chamber adjacent the wall.

The apparatus could further comprise a thermally conductive gasket sandwiched between the sensor and the wall. Said thermally conductive gasket could act as the seal.

The apparatus could further comprise an air-permeable, water-impermeable filter separating said sensor port from said flow channel.

Said wall and said seal could be formed by a two-shot moulding process.

The sensor could comprise a metal housing.

The inhaler could further comprise a data buffer configured to store data received from a sensing element of the sensor. Said data buffer could optionally be comprised in the sensor. Said data buffer could be configured to store data corresponding to one inhalation/exhalation waveform. Said data buffer could be a first in, first out (FIFO) data buffer.

The inhaler could further comprise an additional MEMS barometric pressure sensor configured for monitoring environmental barometric activity.

The inhaler could further comprise a transmitter, receiver or transceiver configured to communicate data from and/or to the sensor. Said transmitter, receiver or transceiver could be a wireless transmitter, receiver or transceiver. Said wireless transmitter, receiver or transceiver could be a Bluetooth™ subsystem, optionally a Bluetooth™ Low Energy (BLE) integrated circuit or System on Chip (SoC). Said transmitter, receiver or transceiver and the sensor could be comprised in a single integrated circuit or SoC.

The sensor could be mounted on a printed circuit board (PCB).

The inhaler could further comprise a battery, optionally a coin cell, arranged to power the sensor.

The sensor could have a sensitivity of 20 Pascals or less.

The sensor could comprise a sensing element. The processor could be configured to poll said sensing element at a frequency of greater than or equal to 100 Hz.

The inhaler could further comprise control means for switching on the sensor and/or waking the sensor from a low power state. The processor could be configured to respond to said control means switching on and/or waking up the sensor by taking a tare reading from said sensing element and calibrating data received from the sensing element subsequently using said tare reading.

The processor could be configured to determine a dynamic zero from a moving average of measurements by the sensor, and dynamically calibrate the sensor according to said dynamic zero.

The processor could be configured to filter out electrical noise inherent to the sensor and/or environmental anomalies in data received from a sensing element of the sensor.

The inhaler could further comprise a temperature sensor, optionally integral with the pressure sensor. The processor, optionally comprised in one of the pressure and temperature sensors, could be configured to apply temperature compensation determined from data received from a sensing element of the temperature sensor to data received from a sensing element of the pressure sensor.

The inhaler could further comprise a mouthpiece, said sensor port being pneumatically coupled to a flow channel in pneumatic communication with said mouthpiece.

The sensor could be configured to collect data for processing to monitor adherence to a dosage regimen and/or compliance of drug delivery.

According to a second aspect there is provided a method of dry powder medicament dosing by means of a tidal inhaler, said method comprising: a miniature pressure sensor of said inhaler, said sensor comprising a sensor port, sensing a change in pressure at said sensor port, the sensor port being pneumatically coupled to a flow channel through which a user can inhale; responsive to said sensing, making a determination that inhalation of a spontaneous breath through said flow channel is in progress; responsive to said determination, issuing a start dosing signal; and in response to receiving said start dosing signal, a dosing mechanism of the inhaler releasing dry powder medicament into the flow channel during inhalation of said spontaneous breath.

The miniature pressure sensor could be a microelectromechanical system (MEMS) pressure sensor or a nanoelectromechanical system (NEMS) pressure sensor.

The determination could be made when said change in pressure at the sensor port indicates that air flow rate in the flow channel has reached a predetermined start dosing threshold value. Said predetermined start dosing threshold value could be programmed into an internal hardware register of the sensor. The determination could be performed by the sensor. Said issuing of the dosing signal could be performed by the sensor. Said predetermined threshold value could be less than 50%, for example between 30 and 35%, for example 32%, of a predetermined peak inspiratory flow (PIF) rate value.

Said releasing could fill one or more discrete time packets. Said discrete time packets could have a duration of approximately 100 ms.

The method could further comprise, subsequent to making the determination that inhalation of a spontaneous breath through said flow channel is in progress, making a determination that a target volume of the user's lungs has been filled. The method could further comprise, responsive to said determination that a target volume of the user's lungs has been filled, issuing a stop dosing signal. The method could further comprise, in response to receiving said stop dosing signal, said dosing mechanism stopping release of dry powder medicament into the flow channel.

The determination that a target volume of the user's lungs has been filled could be made when said change in pressure at the sensor port indicates that air flow rate in the flow channel, averaged over time, is at a predetermined stop dosing threshold value.

The method could be repeated over a plurality of consecutive spontaneous breaths.

The method could further comprise wirelessly transmitting data collected by the sensor, and/or data derived from data collected by the sensor, to a device external to the inhaler.

The method could further comprise: switching on the sensor or waking the sensor from a low power state; in response to the sensor switching on or waking up, taking a tare reading from a sensing element of the sensor; and calibrating data received from the sensing element subsequently using said tare reading.

The method could further comprise: determining a dynamic zero from a moving average of measurements by the sensor; and dynamically calibrating the sensor according to said dynamic zero.

The method could further comprise: monitoring environmental barometric activity using an additional MEMS barometric pressure sensor; and calibrating the sensor having the sensor port pneumatically coupled to the flow channel against said additional sensor.

The method could further comprise storing data received from a sensing element of the sensor in a data buffer. Said data could correspond to one inhalation/exhalation waveform.

The method could further comprise communicating data from and/or to the sensor. Said communicating could be wireless. Said wireless communication could use a Bluetooth™ protocol, optionally the Bluetooth™ Low Energy (BLE) protocol.

The method could further comprise the processor polling a sensing element of the sensor at a frequency of greater than or equal to 100 Hz.

The method could further comprise filtering out inherent electrical noise and/or environmental anomalies in data received from a sensing element of the sensor.

The method could further comprise applying temperature compensation to data received from a sensing element of the pressure sensor using data received from a sensing element of a temperature sensor.

The method could further comprise determining the volume of air inspired or expired by a user of the inhaler from data sensed by a sensing element of the sensor.

The method could further comprise using data sensed by a sensing element of the sensor to monitor adherence to a dosage regimen and/or compliance of drug delivery.

According to a third aspect, there is provided a computer program product comprising instructions for execution by a computer processor to perform the method of the second aspect.

According to a fourth aspect, there is provided an inhaler substantially as herein described with reference to the accompanying figures.

According to a fifth aspect, there is provided a method substantially as herein described with reference to the accompanying figures.

According to a sixth aspect, there is provided a computer program product substantially as herein described with reference to the accompanying figures.

Examples of the present invention will now be described with reference to the accompanying drawings, in which.

Elements shown in the Figures are not drawn to scale, but only to illustrate operation. Like elements are indicated by like reference numerals.

Figure 1:
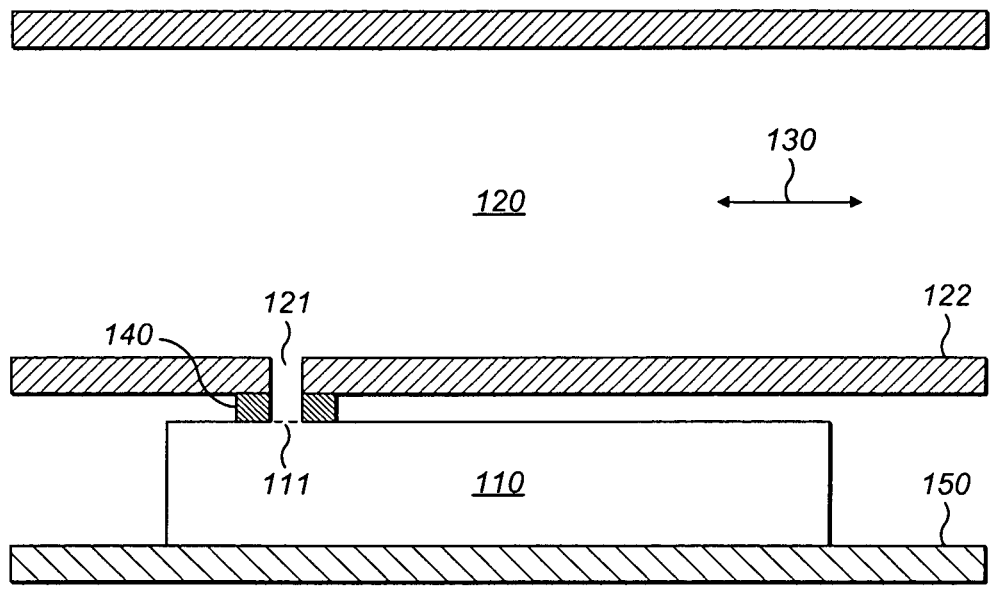
FIGS. 1 to 5 illustrate example arrangements for a miniature pressure sensor for breath detection with respect to a flow channel.

In addition to the differential (two port) type pressure sensors and the single port gauge type sensors, with separate measurements made before and after use, discussed above, absolute or barometric pressure sensors are available. Barometric pressure sensors are referenced to vacuum. They are sometimes referred to as altimeters since altitude can be deduced from barometric pressure readings. Sensors of this type have not been considered for use in breath detection because of their extremely wide range (20 to 110 kPa) and low resolution. Considering how a typical breath profile may generate pressure changes of the order of only 0.2 kPa, this would require operating the sensor over an extremely narrow portion of its operating range.

However, with miniaturisation, including the introduction of MEMS and NEMS technologies, much improved sensors are now available. A typical MEMS barometric sensor is capable of operation from 20 kPa to 110 kPa and can detect the flow rates of less than 30 lpm (litres per minute) typical of adult tidal breathing when pneumatically coupled to a flow path having a known flow resistance.

Using a barometric sensor enables use of the barometric pressure as a baseline throughout the measurement cycle, thereby addressing the uncertainty of other single port approaches.

Also, having knowledge of the local barometric pressure can provide some insight into patient lung function. It is suspected that changes in atmospheric pressure, such as those associated with approaching storm fronts, may have an effect on patient breathing, possibly even related to asthma and COPD events.

Barometric pressure sensors are already in stressed condition, having an integral reference port sealed within the device under vacuum. This means that they have low hysteresis in the region of interest.

Due to the extremely small size and mass of their sensing elements, MEMS sensors are capable of reacting to extremely small pressure changes. Some are capable of resolving pressure changes as low as 1 Pa.

MEMS barometric pressure sensors can include all of the requisite analogue circuitry within the sensor package. Temperature compensation and/or digital interfaces can also be integrated with the pressure sensor.

For example, the Freescale MPL3115A2 MEMS barometer/altimeter chip (pressure sensor) is digital, using an $I^2C$ interface to communicate pressure information to a host micro-computer.

MEMS barometric pressure sensors can be packaged in metal. This provides RF shielding and good thermal conductivity for temperature compensation.

MEMS barometric pressure sensors are also low cost, low power and very small. This makes them especially suitable for use in portable and/or disposable devices which may, for example, be powered by batteries such as coin cells.

The small size of MEMS barometric pressure sensors makes it easy to incorporate them into existing designs of inhalers. It may be easier to incorporate them in or close to a mouthpiece to more accurately measure the pressure change caused by a patient's inhalation or exhalation.

A miniature barometric pressure sensor can be connected directly to the patient airway using only a small hole to the air path which does not require tubing of any kind. This minimizes the possibility of moisture condensation and potential bacterial growth associated with elastomeric tubing. An internal seal, for example a gel seal, can be included to protect the sensor element from contamination.

An example of this type of arrangement is shown in FIG. 1. A miniature barometric pressure sensor 110 is placed against the flow channel 120 through which a patient breathes. Airflow is substantially axial as indicated by arrow 130. The sensor port 111 is sealed in line with an opening 121 in flow channel wall 122 by a pneumatic (airtight) seal 140. (Note that, so long as there is a pneumatic connection between the sensor port and the flow channel, the seal need not be completely airtight.) Sensor port 111 optionally comprises a filter, for example an air-permeable, water-impermeable filter. The flow channel and the seal could be formed by a two-shot moulding process. The pressure sensor 110 can be mounted on a printed circuit board (PCB) 150 to provide connection to power sources and other electronics.

Figure 2:
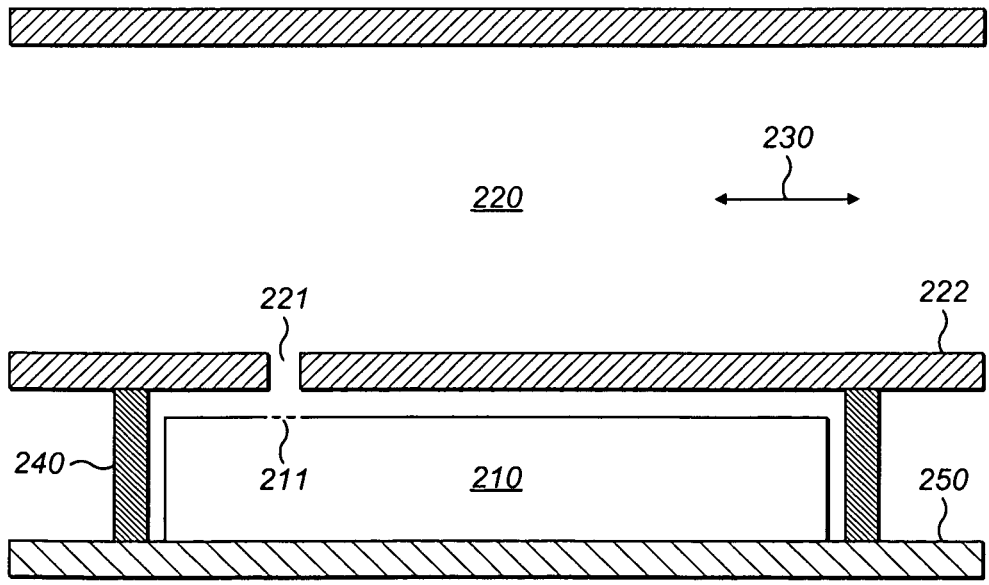

Instead of positioning the seal 140 around the channel between opening 121 and sensor port 111, the entire miniature sensor could be encapsulated within a chamber adjacent to the flow channel as illustrated in FIG. 2. Pneumatic seal 240 is located outside of the sensor footprint and extends all the way from the exterior of flow channel wall 222 to the surface 250 on which the sensor 210 is mounted (for example the component surface of a PCB). FIG. 2 shows a cross-section; pneumatic seal 240 surrounds the perimeter of the sensor 210 whether it is circular, square, rectangular or any other shape. The seal 240, sensor mount 250 and flow channel wall 222 thus form a cavity pneumatically isolated from the external environment except for the flow channel in the location of the opening 221. The pressure at the sensor port 211 is therefore equalised with the pressure in the flow channel at the opening 221.

Since MEMS sensors are available with built-in temperature compensation, there may not be any need for use of external thermal sensors. Compensation can be provided right at the measurement site, increasing the accuracy of the compensation. A MEMS sensor with built-in temperature compensation can also act as a compact breath thermometer, providing further information to the patient and/or their caregiver. If the housing of the sensor is metal, then not only is the sensitive internal circuitry isolated from RF fields, such as those associated with mobile phones or nearby disturbances, but the sensor will also rapidly equilibrate to the local temperature in order to provide optimum temperature compensation.

Figure 3:
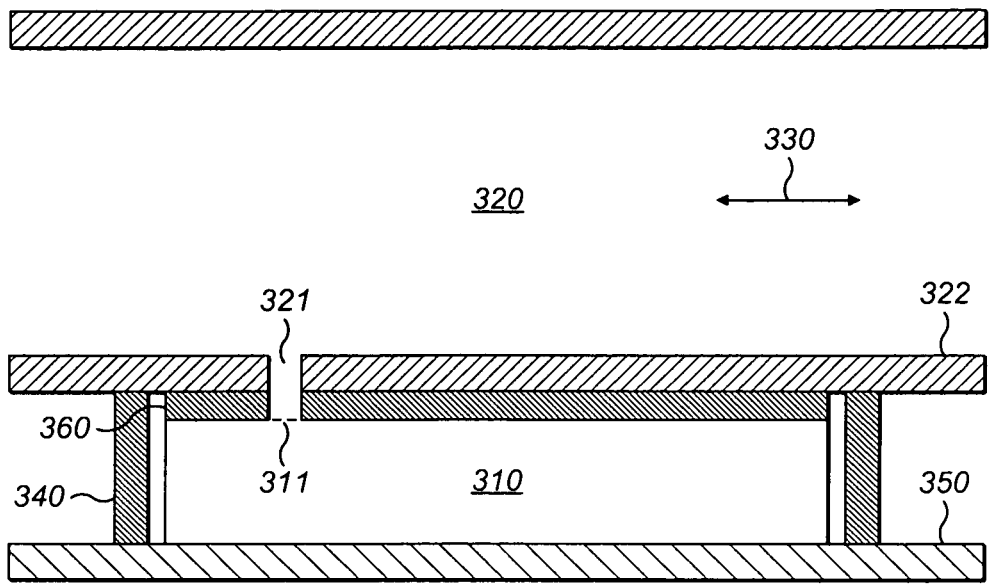

In the embodiments of FIGS. 1 and 2, the miniature sensor is separated from the flow channel wall by an air gap. To improve the ability of the miniature sensor to rapidly detect changes in flow channel temperature, a thermally conductive gasket can be used as shown in FIG. 3. (FIG. 3 is in other respects similar to FIG. 2.)

In the example arrangement of FIG. 3, a thermally conductive gasket 360, such as the silicone types used for transistor heat sinks, is provided between the (optionally metal) housing of the miniature sensor 310 and the flow channel wall 322. The greater the adjacent surface areas covered by the gasket the quicker the temperature equilibration. The gasket 360 could therefore extend over substantially the entire surface of the sensor 310 facing the flow channel wall 322.

Figure 4:
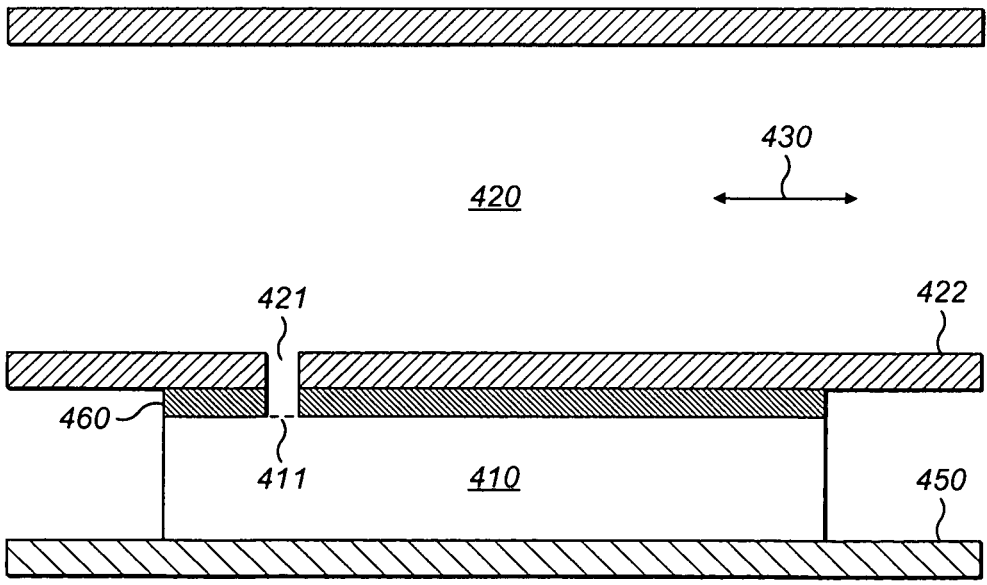

FIG. 4 shows an example arrangement in which a thermally conductive gasket 460 is made of an air-impermeable substance which deforms to the contours of the surfaces of the sensor 410 and flow channel wall 422 it is compressed between. It thus provides a good thermal connection while at the same time acting as a pneumatic seal, eliminating the need for a separate sealing element.

Figure 5:
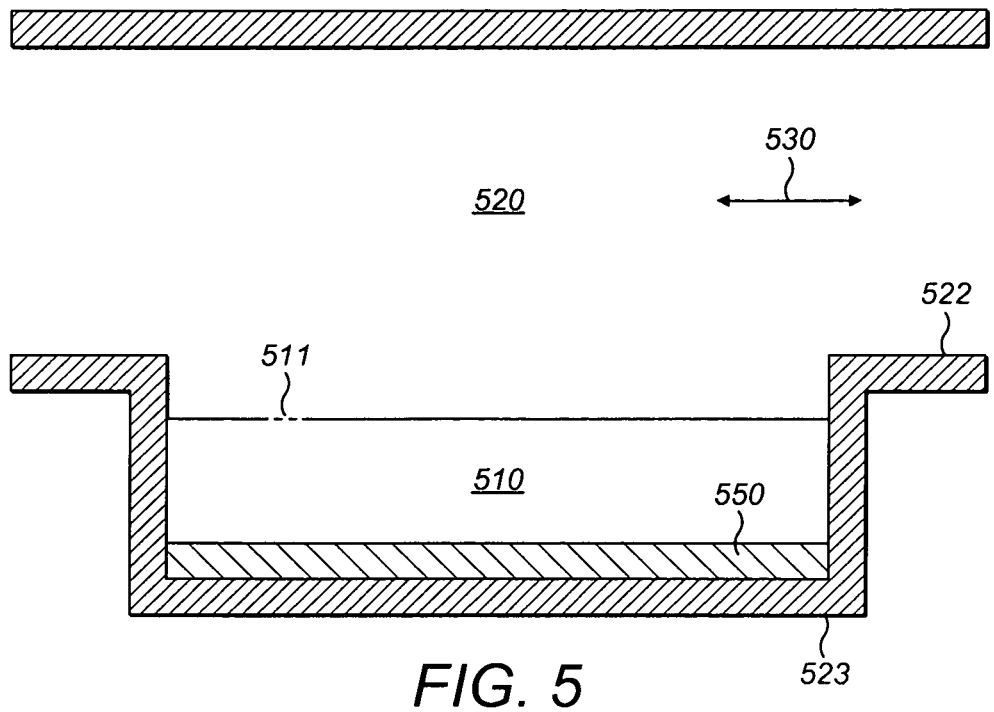

An alternative to positioning the sensor adjacent the flow channel is to place the entire sensor within the low pressure airway of the device to be monitored as illustrated in FIG. 5. For example, the sensor could be placed within the body of a DPI or the 'boot' of a pressurised MDI (pMDI). (The term boot refers to the body of the inhaler that generally holds the drug canister.) In this arrangement the sensor is truly measuring the pressure (and optionally, temperature) of the airflow itself, providing improved accuracy. Therefore there is also no need for any sealing element to create a pneumatic conduit between the flow channel 520 and the sensor port 511, or for any thermally conductive gasket to aid in temperature equilibration between them. It is also not necessary to provide the sensor with any access to the external pressure environment for reference purposes because the reference is already built into the sensor itself in the form of a vacuum reference.

In the example of FIG. 5, the miniature barometric pressure sensor 510 is mounted on the interior of flow channel wall 522, optionally via a PCB 550. The flow channel wall 522 may comprise a recessed part 523 in which the sensor 510 is located as shown to reduce disruption to the airflow indicated at 530. For example, the depth of such a recess 523 could be substantially equal to the thickness of the sensor 510 so that the surface of the sensor comprising the sensor port 511 lies flush with the parts of the interior surface of flow channel wall 522 to either side of the sensor 510. Recess 523 could be a volume cut out of the wall 522 or a part of the wall that extends radially outwards relative to the rest as shown.

It should be noted that due to their small size, miniature pressure sensors can be used to monitor patient flow through, for example, nebulisers, DPIs or pMDIs, thus facilitating low cost compliance monitoring, in addition to/in place of adherence monitoring, which confirms device actuation. Said compliance monitoring could be implemented using an accessory device that couples to the dosing device through a small hole to the airway to be monitored, or in the dosing device itself. The small size, high performance and low cost of MEMS sensors make them ideally suited to such applications where size and weight are major considerations for users who may have to carry their inhaler with them at all times.

For example, the miniature barometric pressure sensor could be in or near the mouthpiece. Alternatively, the miniature barometric pressure sensor could be contained within a module attached to, and in fluid communication with, the inhaler and arranged such that a seal maintains the same pressure between the interior of the module and the inhaler body. The module could optionally comprise one or more of electronics, power and communication means to power and/or control the miniature barometric pressure sensor and/or to transmit readings to a receiver by wired or wireless means. The module could be connected (optionally reversibly) to the inhaler via fastening means and be in fluid communication with the inhaler interior and hence the airflow path via one or more apertures in the inhaler body.

If output from the miniature pressure sensor is digital, all low level signal processing can be done within the sensor, shielding it from outside interference. This makes it possible to work with signals of the order of tens of Pascals without much difficulty, something that traditional sensors with external circuitry would be challenged to do.

Figure 6:
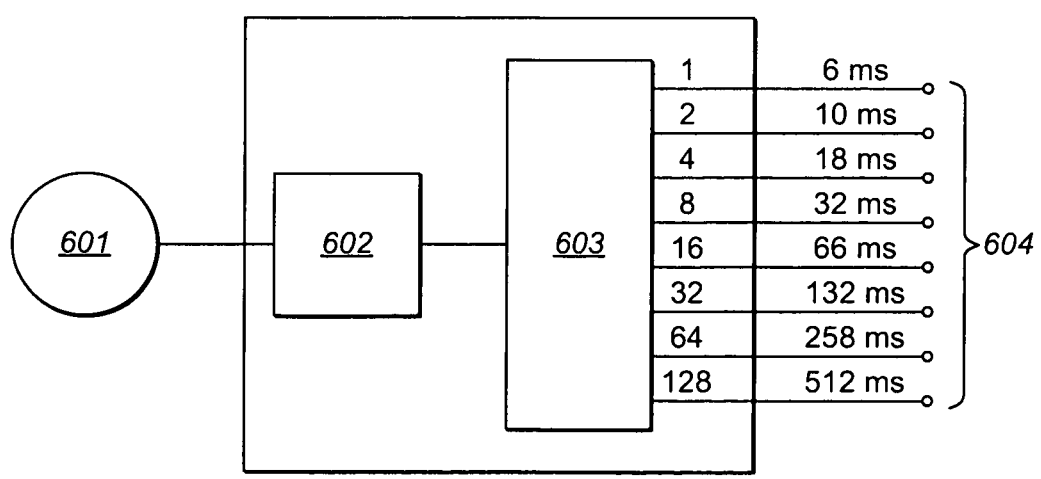
FIG. 6 is a schematic of example sensor electronics.

FIG. 6 shows schematically some electronic components of an example miniature barometric pressure sensor. Sensor element 601 passes analogue signals to analogue to digital converter (ADC) 602. The digital output signal of ADC 602 is then averaged by a rolling average filter over many cycles to reduce noise. Various averages can be selected under program control in order to balance noise against response time.

As one example, block 603 represents a means of selecting one of eight different oversample (i.e. filter) ratios to output at 604. The fastest response is associated with OSR=1, but this is also the noisiest setting. Conversely, OSR=128 introduces the least noise, but has the slowest response. The optimum setting can be chosen depending on the particular application. With an OSR setting of 16, the output is clean enough and the update time quick enough for most respiratory applications.

It may be desired, for example in order to record patient flow profiles, to create a waveform associated with the real time fluctuations of pressure detected by the sensor. If one were to construct such a waveform from single readings of the sensor each time new data became available, the resulting waveform would exhibit blocky artefacts, rather than a smooth waveform, due to the delays associated with each tap. However, by driving the ADC 602 at a suitable frequency, for example approximately 100 Hz, and reading data at the same rate, the data presented to each tap is further averaged, resulting in a much smoother waveform.

The averaged output can then be passed to a circular first in, first out (FIFO) buffer (not shown) for storage until the data can be processed by a connected processor integrated into the device, or transmitted for offloaded processing. Such a FIFO buffer could, for example, store a number of samples approximately equivalent to, or a little greater than, one typical breath waveform to ensure that an entire inhalation/exhalation profile can be captured. Using a buffer reduces the demand on the serial port of the sensor in cases where the waveform is not required in real time.

With the addition of wireless communications it is possible to monitor patient adherence and compliance and communicate such information, for example including patient flow profiles, to a user device such as a smart phone or tablet. From a user device data can optionally be communicated to a caregiver's device, for example a doctor's personal computer (PC). This could be done using a wired connection, for example via a Universal Serial Bus (USB) port. Alternatively, using wireless technology, it is possible to communicate results to the outside world without interrupting the product housing in any significant way. Suitable wireless technologies could include, for example, WiFi technologies such as IEEE 802.11, Medical Body Area Network (MBAN) technologies such as IEEE 802.15, Near Field Communication (NFC) technologies, mobile technologies such as 3G and Bluetooth™ technologies such as Bluetooth™ Low Energy (BLE). A wireless transceiver, for example in the form of a BLE chip, could be connected to the miniature sensor or integrated with it.

Such wireless connectivity could be used, for example, to report device actuation and/or sensed inhalation with date and time stamps in real time. This data could be processed externally and if the result of such processing is that it is determined that a prescription should be refilled, an alert can be sent to the patient and/or caregiver and/or pharmacist. Alerts could be provided via one or more user interfaces of the inhaler (for example an LED and/or a buzzer) or via text message or email. As another example, if no dosing report is received within a predetermined period following a scheduled dosing time, a reminder could be sent to the patient and/or caregiver. Alerts could also be generated for example if use frequency is exceeding a safe threshold.

Alternatively, a wired connector could be provided on an inhaler comprising a miniature pressure sensor as described for transfer of data between the sensor and patient and/or caregiver devices.

Aerosol delivery from nebulisers can be targeted to specific areas of the lung by way of regulating inspiratory flow rate. For example, drug can be released to the patient during a prolonged inhalation at a flow rate fixed in the 18 to 20 lpm range by a specially formed high resistance mouthpiece. By controlling the flow rate of air entering the lungs, it is possible to exclude certain areas from drug delivery by filling them first with fresh air and then, once full, activating the aerosol generator so that areas of the lung yet to be filled can receive medication.

Predictability in such systems depends on having a regulated flow rate during inspiration, something that is difficult for most patients to achieve on their own, and impossible in some cases, for example for very young children. By purposely introducing a restriction through which the patient breathes, a certain amount of flow rate regulation can be implemented which then allows some control over lung filling to be exerted. For optimum lung deposition, such techniques require patients to perform a single inhalation lasting for several seconds. However, for some patients, neither airway restrictions nor extended inhalations can be tolerated.

In addition, breathing through a restriction has the potential to create negative pleural pressure, something that can actually close off the smaller airways, and potentially those parts of the lung being targeted.

The extended inhalation required by these systems may also be difficult for some patients. Dry powder inhalers can aerosolise medication quicker than aqueous nebulisers. Dry powder medication also tends to be more concentrated than aqueous solutions. Accordingly, extended inhalation may not be required for dry powder inhalers.

The extended inhalation and restrictions required for flow regulation are not appropriate for use in a tidal inhaler, which by definition requires nothing more of the patient than simple tidal breathing. For such applications, timed drug delivery in discrete packets as discussed below may provide particular benefit.

Looking at any point on an inspiratory tidal flow curve, the flow would seem to be changing rapidly, thus making it unsuitable for targeted drug deposition. However, across very small periods of time the flow is in fact relatively constant. Therefore, by delivering metered doses of dry powder into these very brief time slots it is possible to accomplish the benefits of targeted drug deposition using normal tidal breathing. Drug is still released during periods of constant flow, but the specific area of the lung to be targeted can be dosed over the course of several breaths. This method both frees the patient from performing a single long inhalation, and eliminates the need for a restricted mouthpiece.

For this method to work reliably, the inhaler has to release drug in discrete packets at precisely the same point on the inhalation curve from one breath to the next. Since said curve can change more easily when not using a restricted mouthpiece, that point would have to be a very specific flow. This is possible using a miniature pressure sensor. Using a miniature pressure sensor to determine flow rate means that changes in the patient's breathing pattern are automatically accommodated since drug can always be released at the same flow rate.

When pressure sensing is used to determine timing of drug delivery, a key parameter to consider is the peak inspiratory flow (PIF), which defines the point at which inspiratory flow begins to decrease. PIF also corresponds to the maximum pressure change and therefore informs the required operating range of the sensor. For purposes of respiratory drug delivery, it is important to introduce drug to the patient prior to reaching PIF, mainly because much of the lung volume has already filled by that time. It can be desirable to release drug as early in the inspiratory cycle as possible, taking into account the time required to aerosolise the drug and present it to the patient airway for entrainment.

Healthy adults typically exhibit peak inspiratory flows of ≥30 lpm while COPD adults exhibit even higher flows. Adult cystic fibrosis (CF) sufferers exhibit slightly lower peak flows of around 16 to 19 lpm. Thus the peak flows a sensor device should be able to deal with range from 16 to 60 lpm.

It should be noted that the above data was obtained from a review of various studies which used little if any airway resistance. In any kind of inhaler there will always be some amount of resistance to airflow. In fact, devices that use pressure sensors to determine patient flow actually depend on this resistance in order to generate the pressure drop to be measured. Recognising that some amount of resistance is needed, but absent any data on sensitivity to this parameter for COPD patients, it is appropriate to use a resistance small enough to be comfortable to the patient, yet large enough to generate the required pressure drop. An R value of approximately $0.06$ $cmH20^{0.5}/lpm$ is appropriate.

The above data illustrates the range of peak inspiratory flows associated with patients breathing at rest, and does not represent the flows at which aerosol should be delivered. If anything, it represents the flows at which aerosol delivery should stop. The actual point of aerosol generation should occur earlier in the inspiratory cycle when the lungs are still filling.

Now that peak flow rates have been established for the range of patients likely to be encountered, a suitable trigger threshold can be identified. Peak flow for a typical adult is around 30 lpm, with around 15 lpm for a typical child. If the aerosol generator were to trigger at say 12 lpm, drug would be released roughly one third of the way to PIF for the adult but closer to two thirds to PIF for the child. This suggests that a fixed threshold might release drug too late in the inspiratory cycle for patients with lower PIF values.

While it may be possible to use a lower trigger threshold to accommodate such patients, an alternative approach might be to monitor the patient breathing for one, two or more cycles. This could be done as a one-time "inhaler personalization" routine, could be periodically updated, for example at a doctor's appointment or in response to a reminder provided to the patient by an indicator on the device or in an email or text message, or (provided the dosing is not intended as a time-critical emergency response, for example to an asthma attack) each time the patient takes a dose. The closer the personalization routine is performed to dosing, the more likely it is that the patient's breathing pattern during dosing will match that during personalization, and thus the more accurate the targeting. In this manner, individual PIF values could be determined and an appropriate fixed threshold established for that particular patient and PIF. This 'variable threshold' approach allows the threshold to be some percentage of PIF for any given patient. If subsequent PIFs fall too close to the fixed threshold so determined, the inhaler could be prevented from triggering and alert the patient of a low flow condition. In this case, the patient would have to breathe harder in order to receive treatment. In fact, since the threshold would be based upon the actual patient inhalation history, they would only have to breathe as they did when that history was established.

While always triggering the aerosol generator at a certain point on the inspiratory curve, as facilitated by the variable approach described above, ensures consistent dosing, the complications involved may not be necessary if a low enough trigger can be achieved. If a reliable trigger could be achieved at say 50% of the typical child PIF, that same trigger would occur even earlier for an adult patient. So another approach would be to make the trigger as low as possible for the lowest patient PIF expected. Based on the data presented above, this would appear to be around 16 lpm.

In the paragraphs that follow, consideration will be given to both the variable as well as fixed thresholds to see what can be accomplished. It should be noted that because MEMS barometric pressure sensors respond to environmental barometric pressure, which can change over time, attention should be paid to the initial reading that any subsequent trigger is based upon. An automatic zero reading (i.e. tare) could be performed immediately prior to monitoring any inhalation signal. While it is possible for this value to change over time in response to changes in local environmental barometric pressure, it would not be expected to cause any issues if a treatment is completed within a few minutes. Alternatively, a second barometer chip could be used to keep track of barometric activity, allowing the primary chip to be used exclusively for breath detection.

It should be noted that whatever the detection threshold may be, it can be implemented either in software or hardware. The former can be implemented using software running on a micro controller which collects pressure data from the sensor in real time. The latter on the other hand, avoids the need for such a volume of digital communications between the sensor and micro controller by programming an internal hardware register with the threshold value and using a built in interrupt capability of the device to signal when that threshold has been reached. In this way, the host microcontroller sets the threshold in the device and waits for the interrupt to occur without the need for further communication with the device. For example, the sensor could be set to generate an interrupt whenever a pressure change of 20 Pa or greater is detected. If the sensing element is polled at a frequency of approximately 100 Hz, an internal filter of the sensor will have sufficient samples for its internal averaging to produce an output distinguishable from noise.

In addition to flow rate, volume should be considered. If the flow rate used to trigger aerosol release occurs at a time when most of the inhaled volume has already occurred, little of the drug will make it to the lungs. This is because approximately the last 150 cc (in adults) would possibly not even reach the Alveoli. Rather, it would fill the anatomical dead space associated with the trachea and larger airways. Once PIF is reached, approximately 0.6 l of the total 0.7 l has already been inhaled by adult subjects. This represents 85% of the volume inhaled in just one breath. In other words, by the time PIF has been achieved, only 15% of the tidal volume remains to be inhaled.

Figure 7:
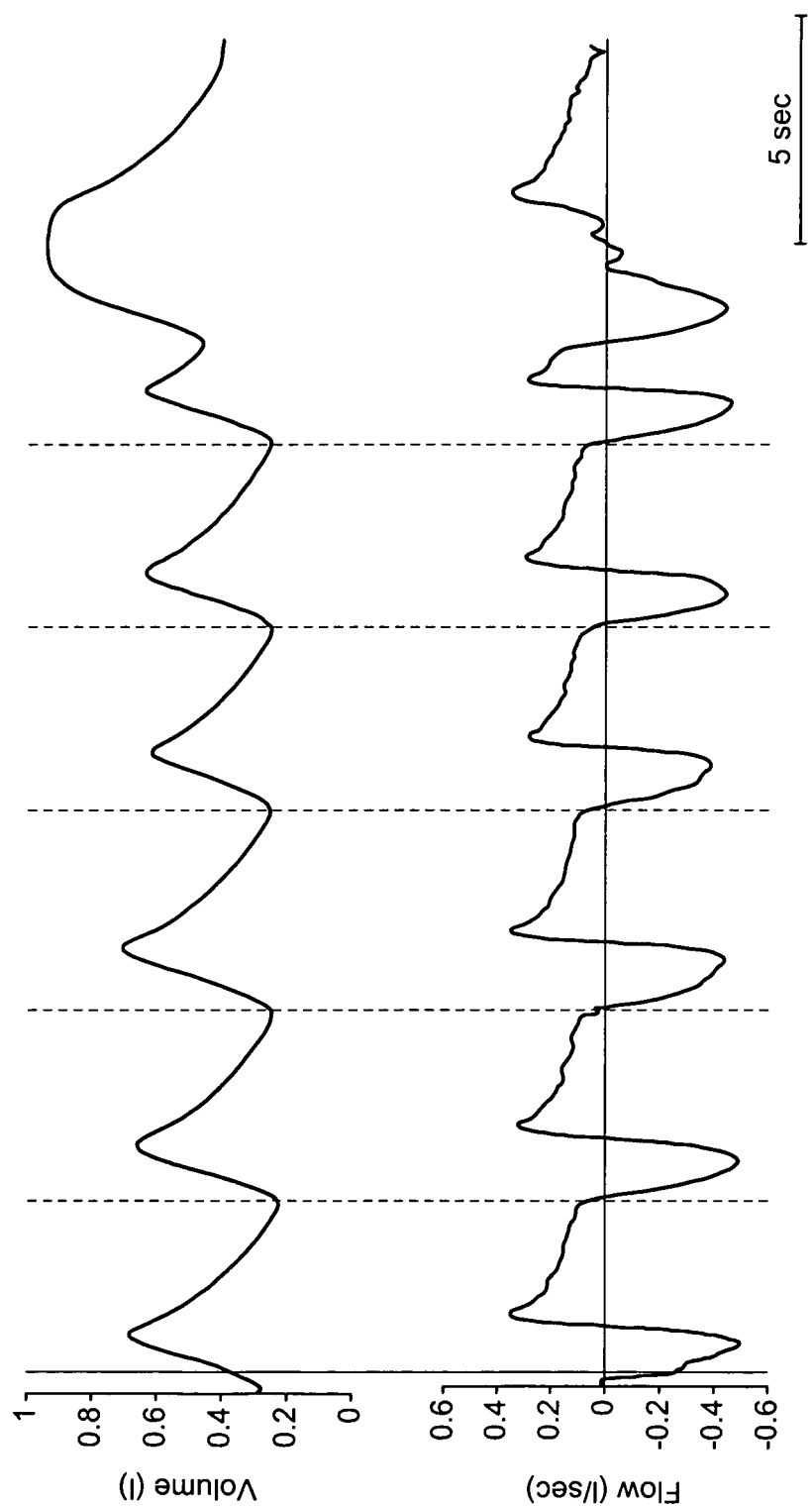
FIG. 7 illustrates the relationship between flow and volume during spontaneous breathing in elderly patients with COPD.
Figure 8:
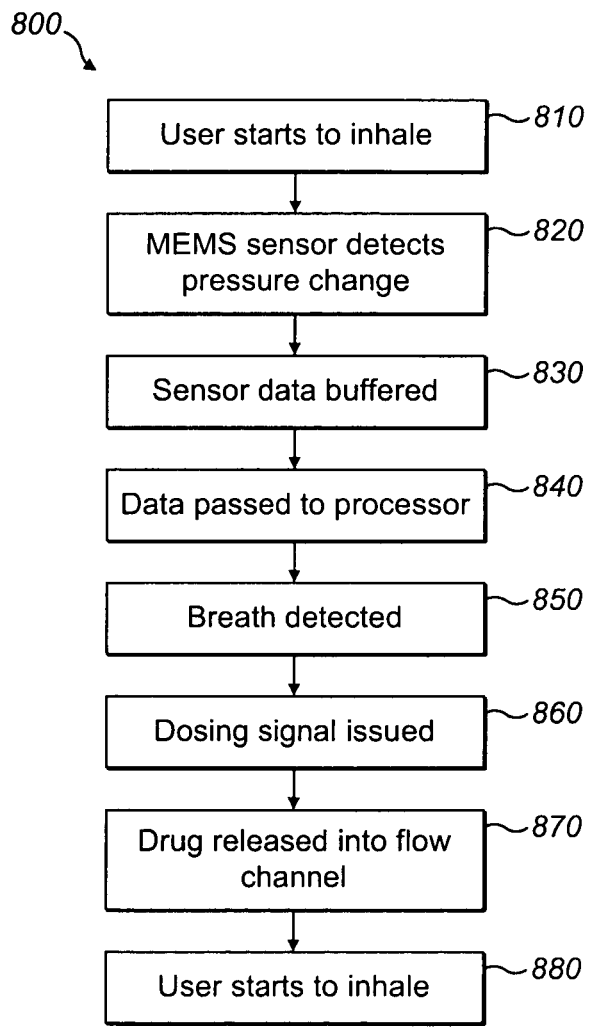
FIG. 8 is a flowchart illustrating an example drug dosing method.

FIG. 7 (based on "The relationship between spontaneous expiratory flow-volume curve configuration and airflow obstruction in elderly COPD patients", Nozoe et. al, RESPIRATORY CARE Paper in Press, 9 Apr. 2013) illustrates the relationship between flow and volume during spontaneous breathing in elderly patients with COPD. FIG. 7 shows an arbitrary trigger point about half way to PIF, at roughly 2.5 lps (litres per second), denoted by the solid vertical line running through the first section of both traces. The line intersects the volume trace at roughly 0.36 l, which represents 0.36/0.7=51% of the total volume inhaled in one breath. In other words, roughly half of the volume of a single breath has already been inhaled. This suggests that any trigger point based upon inspiratory flow should be limited to 50% of PIF or less.

An important limitation of any respiratory drug delivery system which should be considered is the time it takes for the aerosol/powder generator to respond to its trigger. By way of example, consider a nebuliser which delivers aerosol in discrete packets, each 100 ms in duration and limited to just one per breath. Assume that it requires roughly 40 ms to eject aerosol from the time the aerosol generator is first activated (i.e. triggered). Assume also that the highest respiration rate is approximately 33 BPM (breaths per minute), where each breath lasts 1.8 seconds. Assuming an I:E (inhalation to exhalation) ratio of 1:3, an inhalation would then last 1.8/4=450 ms. The time to reach PIF is then roughly half of this, or 225 ms. This means that if aerosol generation is triggered half way to PIF, which in this example is 113 ms, aerosol would not actually be released until 40 ms later, or at 153 ms. This is 153/225=68% of the way to PIF. This would be late in terms of aerosol generation, especially since the aerosol is released over 100 ms. In this case aerosol generation would stop at 153+100=253 ms, or only 28 ms past PIF. This may still be acceptable, but in order to actually release drug (as opposed to triggering) half way to PIF, the trigger should be approximately (113−40)/225=32% to PIF. In this case, aerosol generation would stop at 85+100=173 ms, which is 52 ms from PIF.

For an inhaler that releases medication in discrete packets, it is possible to emulate the targeted drug deposition mode of the breath actuated nebulisers mentioned above by adjusting the trigger point. This avoids the need for the patient to take an extended breath at a particular regulated flow rate. If drug packets are dispensed early in the inspiratory cycle they flow deep into the distal regions of the lungs. If released late in the cycle, they flow into only the upper part of the lungs. If released anywhere in between, intermediate areas of the lung will be targeted. Provided that the inspired flow rate is relatively constant over the period of drug delivery, it is possible to target drug delivery to different parts of the lung by controlling the specific time and duration of each packet release. In this manner, it is possible to emulate the therapy of flow-restricted targeted drug deposition breath actuated nebulisers using simple tidal breathing. This makes targeted drug delivery available to babies, small children, and patients unable to take extended breaths for any other reason.

Dry powder medication for such an inhaler could be packaged in blisters containing the correct quantity of medication for a single dose. This could be released over several, for example 5 to 10, inhalations by activating a piezoelectric vibrator once per inhalation.

It should be noted that a trade-off exists between any trigger threshold and internal pressure noise generated by the barometer chip. As the trigger threshold is adjusted to lower and lower flows (i.e. pressures), a point is reached where the pressure noise generated within the chip begins to look like an actual breath signal, introducing the potential for false triggers. When capturing actual breathing waveforms, this same noise causes variability in the observed trigger position. Also, since this chip is a barometer, the lower the trigger threshold, the more potential exists for rapid environmental changes to look like actual signals. This problem can be mitigated by filtering these anomalies in software.

A trigger threshold of 5 lpm with a rolling average of 10 to 20, for example 12 samples works well in this context (using a resistance of 0.049 $cmH2O^{0.5}$/lpm). Applying the 32% trigger discussed above would limit us to PIFs of 5 lpm/0.32=15.6 lpm. Since this is lower than the 16 lpm identified earlier for CF patients, it is possible to use this as a fixed threshold. However, it is also possible to implement a variable threshold based upon individual patient PIFs if desired.

A variable trigger threshold can be advantageous in treating different diseases and medical conditions. Certain diseases (including Chronic Obstructive Pulmonary Disease (COPD), Cystic Fibrosis (CF) and asthma) that are characterised by narrowing of the larger airways, tend to enhance drug deposition in these same areas through impaction. This is because impaction increases with increasing flow rate and local flow rates are increased by narrowed airways. Although for some topical drugs this can be desirable from a delivery standpoint, the loss of drug through impaction in the larger airways also reduces the amount of drug available for the lung in the periphery (alveoli). Further, any drug that does reach the lung periphery won't stay there very long because the higher flow rates reduce the time available for sedimentation and diffusion, the main methods of deposition in the periphery.

Most inhalers require high flow rates to deliver drug to the patient. However, such high flows encourage impaction and therefore drug deposition in ways that cannot be controlled.

Tidal inhalers on the other hand, work at much lower flow rates, thus reducing impaction loss. In general, the lower the flow rate the less drug will be lost to impaction in the mouth and throat, leaving more drug available for loss through purposeful impaction to the restricted upper airways (e.g. in COPD, CF or asthma patients) or, in the case where no such restrictions are present (e.g. in emphysema patients) to the lung periphery. By controlling the flow rate at which drug release is started and/or stopped, drug can be targeted at different parts of the lungs. Wastage of the drug by impaction on non-target sites is also reduced, thus less drug is required and the drug-containing part of the inhaler, for example the blisters, can be made smaller. Since inhalers are often required to be carried at all times, such size reduction is desirable. This is a particular advantage where disposable drug cartridges are provided separately from a reusable inhaler body since the cartridges can be made smaller and lighter, reducing delivery costs and allowing for more efficient packing.

As another example, if an obstruction (e.g. a tumour) is blocking part of the upper airways and drug delivery is desired past the obstruction deeper into the lungs, the drug can be released at a lower flow rate to minimise the loss of drug to that tumour through impaction. On the other hand, if drug delivery directly to the tumour is desired, drug could be released at a higher flow rate, which would maximise impaction directly onto the tumour.

Such accurate on-the-fly targeting is possible in a dry powder inhaler where the response time of the drug release mechanism (for example a piezoelectric vibrator producing a burst of fine powder from an agglomerated powder bolus) is relatively fast. Liquid nebuliser technology does not permit fast enough response since significantly more time is required to extrude liquid through a mesh to aerosolise it. As one example, certain ultrasonic liquid type nebulizers have a delay time of nebulization after the beginning of ultrasonic vibration of 0.4 seconds, which is an order of magnitude higher than that associated with typical dry powder inhalers. As another example, U.S. Pat. No. 5,515,841A describes a delay in nebulization associated with mesh type liquid nebulizers involving droplets forming on the mesh, said droplets having to be cleared before nebulization can begin. Such issues are not present in dry powder inhalers.

The use of variable trigger points means that, in an inhaler comprising a reusable part and a disposable drug cartridge, different drugs with different target regions can be attached to the same device. Different cartridges could, for example, be identified electronically, either by direct connection or using a wireless technique. Direct connections could include logic such as pull-up resistors or jumpers or non-volatile memory such as Electrically Erasable Programmable Read-Only Memory (EEPROM) or Flash that can be read by the reusable part. Wireless connections can include BLE, or Near Field Communications (NFC) e.g. Radio Frequency Identifier (RFID) tags.

Further, with variable trigger points, the target can be changed on the fly. For instance, a small amount of drug could be delivered to one part of the lung and a larger amount to another, over the course of several tidal inhalations. This could facilitate some novel treatments that could not be implemented using a single, long inhalation. For instance, it may be desired to target a certain area deep in the lungs that is blocked by a restricted area higher up in the lungs. By adjusting the trigger point between inhalations it is possible to, on a first inhalation, use an inhaled drug released at a relatively high flow rate to open those airways that are blocking the target area, and then, on a second inhalation, deliver the remaining dose to the more distal target area at a relatively low flow rate.

Depending on the complexity of the miniature barometric pressure sensor chip used, the chip itself could generate the dosing trigger signal based upon its own monitoring of the pressure readings. As described earlier, programmable thresholds set by a host processor could set the actual trigger point. It might also be possible to program the airway resistance in similar fashion, thus allowing a single chip to be adapted to multiple inhaler applications, each with their own unique resistance values. The chip storing an entire waveform within its FIFO for later retrieval would free the host processor from having to capture this information in real time, allowing it to complete other tasks.

A wireless scheme (for example comprising a BLE module) could be used to transmit patient flow profiles to an app which could then calculate specific breathing parameters. The inhaler could thereby offload the processing required for such a task to, for example, a smart phone processor. Key results identified by such an app, such as respiratory rate (RR), PIF, etc. could then be fed back to the inhaler. Another advantage of such an "app approach" would be offloading the processing of patient data from the drug delivery device to the app, thus reducing hardware needs and facilitating the smallest form factors possible for the inhalers. A further advantage of this approach is that software running on a smart phone, such as app software, can be changed more readily than software running on an inhaler.

In addition to the inhaler functions described above, a spirometer function for an inhaler could be developed using a MEMS barometric pressure sensor. For example, a chip such as the MPL3115A2 barometer chip, in addition to providing the real time pressure updates needed for tidal inhaler applications, can automatically record the maximum and minimum pressures it detects. This could be used in a low cost DPI or pMDI performance monitor, providing simple assessment of the peak pressures (and therefore flows) achieved by the patient with such devices. To use the chip in this application a simple processor can be used to 1) reset the max/min pressure registers prior to use; 2) capture the current barometric pressure as a "tare" reference; 3) monitor the manoeuvre to be measured; and 4) read back the registers. The difference between these final register readings and the tare reading represents the peak expired or inspired pressure. From these and the known resistance of each device, the actual peak flow rates and volumes (inspired and expired) could be calculated. Such functions could for example be provided by a BLE module during down times when not being used for communications.

As another example, inspection of the tidal expiratory flow curve can be used to predict forced expiratory volume in 1 second (FEV1), and therefore airway obstruction, without the need for the forced expiratory manoeuvres typical of traditional spirometry. FEV1 can be determined based upon post peak expiratory flow information obtained during normal tidal breathing. Therefore, by capturing a patient's expiratory flow profile during normal tidal breathing, even during drug delivery, it is possible to assess airway obstruction in real time. In addition to treating the patient, an inhaler could thereby also determine the effectiveness of said treatment over time, possibly leading to improved outcomes.

FIG. 8 is a flow chart of an example method 800 of drug dosing by means of an inhaler. At step 810, a user starts to breathe through a mouthpiece. At step 820, a miniature barometric pressure sensor comprising a sensor port pneumatically coupled to the mouthpiece senses a change in pressure at said sensor port. At step 830, sensed data is stored in a data buffer. At step 840, sensed data is passed to a processor. At step 850, said processor determines that inhalation is in progress. At 860, responsive to said determination, a dosing signal is issued by a controller. At 870, in response to receiving said dosing signal, a dosing mechanism of the inhaler releases a drug into the flow channel. At step 880, the inhalation is complete and the user exhales. All steps of method 800 occur during a single tidal respiratory cycle.

Method 800 could be preceded by opening of a single dose medicament container such as a blister. The blister could be entirely emptied during step 870. Alternatively, method 800 could be repeated over a consecutive series of respiratory cycles, with a portion of the contents of the blister being administered to the user during each inhalation until the blister is emptied after, for example, 6 or 7 inhalations.

The above description relates to exemplary uses of the invention, but it will be appreciated that other implementations and variations are possible.

In addition, the skilled person can modify or alter the particular geometry and arrangement of the particular features of the apparatus. Other variations and modifications will also be apparent to the skilled person. Such variations and modifications can involve equivalent and other features which are already known and which can be used instead of, or in addition to, features described herein. Features that are described in the context of separate embodiments can be provided in combination in a single embodiment. Conversely, features which are described in the context of a single embodiment can also be provided separately or in any suitable sub-combination.

The invention claimed is:

1. A tidal dry powder inhaler comprising:
 a barometric pressure sensor;
 a flow channel through which a user can inhale;
 a sensor port of the barometric pressure sensor, wherein the sensor port is pneumatically coupled to the flow channel;
 a processor configured to:
  determine that a first inhalation and exhalation of tidal breathing by the user has occurred through the flow channel based on measurements received from the barometric pressure sensor;
  determine that a second inhalation of the tidal breathing by the user through said flow channel is in progress based on measurements received from the barometric pressure sensor; and
  generate a variable start dosing signal in response to determining that the second inhalation of the tidal breathing is in progress, wherein the variable start dosing signal is based on the measurements received from the barometric pressure sensor during the first inhalation and exhalation of tidal breathing by the user; and
 a dosing mechanism configured to receive the variable start dosing signal and release dry powder medicament into the flow channel during the second inhalation of the tidal breathing based on the variable start dosing signal.

2. The inhaler of claim 1, wherein the variable start dosing signal is based on a peak inspiratory flow (PIF) of the first inhalation and exhalation of tidal breathing by the user.

3. The inhaler of claim 1, wherein the processor is configured to:
 determine a dynamic zero from a moving average of measurements received from the barometric pressure sensor; and
 calibrate the barometric pressure sensor according to the dynamic zero.

4. The inhaler of claim 1, wherein the dosing mechanism is configured to release dry powder medicament in discrete time packets having a duration between 50 ms to 500 ms.

5. The inhaler of claim 1, wherein:
 the processor is further configured to, subsequent to making the determination that the second inhalation of the tidal breathing is in progress, process measurements received from the barometric pressure sensor to make a determination that a target volume of the user's lungs has been filled;
 the processor is further configured to, responsive to the determination that a target volume of the user's lungs has been filled, issue a stop dosing signal; and
 the dosing mechanism is further configured to stop releasing dry powder medicament into the flow channel in response to receiving the stop dosing signal.

6. The inhaler of claim 5, wherein the processor is configured to make the determination that a target volume of the user's lungs has been filled when measurements received from the barometric pressure sensor indicate that an air flow rate in the flow channel, averaged over time, is at a predetermined stop dosing threshold value.

7. The inhaler of claim 1, comprising a reusable part and a replaceable drug cartridge.

8. The inhaler of claim 7, wherein the reusable part comprises electronic cartridge identification means.

9. The inhaler of claim 1, wherein the barometric pressure sensor is a microelectromechanical system (MEMS) barometric pressure sensor or a nanoelectromechanical system (NEMS) barometric pressure sensor.

10. The inhaler of claim 1, wherein the barometric pressure sensor comprises a thermometer; and
 wherein the processor is further configured to use feedback from the thermometer of the barometric pressure sensor to determine that the second inhalation of the tidal breathing through said flow channel is in progress.

11. The inhaler of claim 1, wherein the barometric pressure sensor comprises a thermometer configured to detect temperature of the user's breath through the flow channel; and
 wherein the processor is further configured to provide information to the user or their caregiver based on the temperature of the user's breath.

12. A method of dry powder medicament dosing using a tidal inhaler, the method comprising:
 determining that a first inhalation and exhalation of tidal breathing by a user has occurred through a flow channel of the tidal inhaler based on measurements received from a barometric pressure sensor, the barometric pressure sensor being pneumatically coupled to the flow channel of the inhaler through an inhaler port of the miniature pressure sensor;
 determining that a second inhalation of the tidal breathing through the flow channel of the tidal inhaler is in progress based on measurements received from a barometric pressure sensor;
 generating a variable start dosing signal in response to determining that the second inhalation of the tidal breathing is in progress, wherein the variable start dosing signal is based on the measurements received from the barometric pressure sensor during the first inhalation and exhalation of tidal breathing by the user; and releasing dry powder medicament into the flow channel using a dosing mechanism during the second inhalation of the tidal breathing based on the variable start dosing signal.

13. The method of claim 12, wherein the variable start dosing signal is based on a peak inspiratory flow (PIF) of the first inhalation and exhalation of tidal breathing by the user.

14. The method of claim 13, wherein the variable start dosing signal is a percentage of the PIF of the first inhalation and exhalation of tidal breathing by the user.

15. The method of claim 12, wherein the releasing the dry powder medicament into the flow channel during the second inhalation of the tidal breathing fills a discrete time packet having a duration between 50 ms to 500 ms.

16. The method of claim 12, further comprising:
subsequent to making the determination that the second inhalation of the tidal breathing is in progress, determining that a target volume of the user's lungs has been filled;
issuing a stop dosing signal upon determining that a target volume of the user's lungs has been filled; and
stopping, via the dosing mechanism, release of dry powder medicament into the flow channel in response to receiving the stop dosing signal.

17. The method of claim 16, wherein the determination that a target volume of the user's lungs has been filled is made when the change in pressure at the sensor port indicates that air flow rate in the flow channel, averaged over time, is at a predetermined stop dosing threshold value.

18. The method of claim 12, further comprising:
switching on the barometric pressure sensor or waking the barometric pressure sensor from a low power state; and
in response to the barometric pressure sensor switching on or waking up, dynamically calibrating the barometric pressure sensor according to the dynamic zero.

19. The method of claim 12, further comprising:
determining a dynamic zero from a moving average of measurements received from the barometric pressure sensor; and
calibrating the barometric pressure sensor according to the dynamic zero.

20. A tidal dry powder inhaler comprising:
a miniature pressure sensor;
a flow channel through which a user can inhale;
a sensor port of the miniature pressure sensor, wherein the sensor port is pneumatically coupled to the flow channel;
a processor configured to:
determine whether tidal breathing through a flow channel of the inhaler is in progress based on measurements received from the miniature pressure sensor;
determine that an inhalation of the tidal breathing is in progress based on measurements received from the miniature pressure sensor;
send a start dosing signal to a dosing mechanism upon determining that an inhalation of the tidal breathing is in progress that causes the release of dry powder medicament into the flow channel;
determine that a target volume of the user's lungs has been filled; and
cause the dosing mechanism to stop the release of the dry powder medicament into the flow channel in response to the determination that the target volume of the user's lungs has been filled.

* * * * *